US00PP14867P3

(12) United States Plant Patent
Hasegawa

(10) Patent No.: US PP14,867 P3
(45) Date of Patent: Jun. 8, 2004

(54) HYBRID CARNATION PLANT NAMED 'CFPC ESSENCE'

(50) Latin Name: *Dianthus caryophyllus*
Varietal Denomination: CFPC Essence

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,117

(22) Filed: Jul. 29, 2002

(65) Prior Publication Data

US 2004/0019938 P1 Jan. 29, 2004

(51) Int. Cl.[7] ..... A01H 5/00
(52) U.S. Cl. ..... Plt./273
(58) Field of Search ..... Plt./273

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of carnation plant producing attractive light yellow picotee pink flowers.

1 Drawing Sheet

Figure 1:
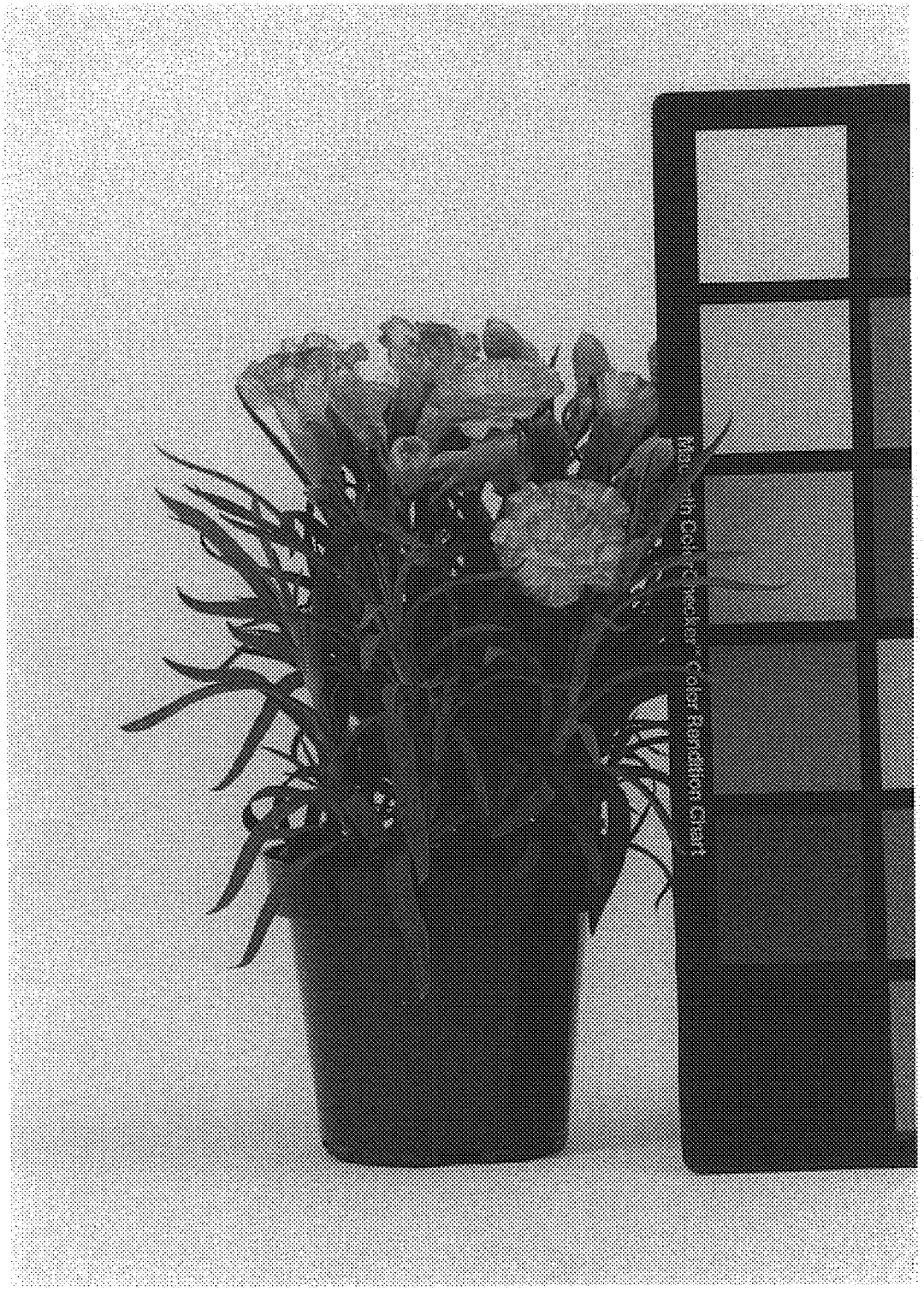

Classification: The present invention relates to a new Hybrid *Dianthus caryophyllus* plant.

Variety denomination: The new plant has the varietal denomination 'CFPC ESSENCE'.

BACKGROUND OF THE INVENTION

The present invention relates to a new and distinct variety of carnation plant. The varietal denomination of the new variety is 'CFPC ESSENCE'. The parents of the new variety are not known. It is the result of open pollenation by unknown seedlings.

SUMMARY OF THE INVENTION

Among the novel characteristics possessed by the new variety which distinguish it from other varieties of which I am aware, are its attractive light yellow picotee pink flowers which retain color without fading. When grown in a greenhouse in Salinas, Calif., in 4½ inch plastic pots, pinched plants are about 7 inches tall and about 7 inches in diameter. Flower diameter averages about 2⅛ inches with a crown of about 1 inch (average). Foliage is about 3¼ inches long and about 7/16 inch wide at its widest point.

Asexual reproduction by propagation by cuttings of the new variety as performed in Salinas, Calif., shows that the foregoing and other distinguishing characteristics come true to form and are established and transmitted through succeeding propagation.

BRIEF DESCRIPTION OF ILLUSTRATION

The accompanying illustration shows a typical specimen of the vegetative growth and flowers of the new variety depicted in color as nearly true as it is reasonably possible to make the same in color illustration of this character.

DESCRIPTION OF THE NEW VARIETY

The following is a detailed description of the new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:

*Botanical.*—Hybrid *Dianthus caryophyllus.*

*Commercial.*—Carnation, standard disbud, type, suitable for cut flower production and as a pot spray.

Plant:

*Height.*—About 7 inches.

*Form.*—Herbaceous.

*Growing habit.*—Semi-upright.

*Blooming habit.*—As a spray (pot).

*Blooming season.*—Year round.

*Rooting time/habit.*—About 18 days.

*Breaking action.*—Average free-breaking plant habit (about 15 breaks per plant) with strong straight stems.

*Mutation prone.*—No.

*Disease resistance.*—Good, resistance to soil-borne diseases such as *Fusarium oxysporum,* and *F. graminearum* and root-rots such as damping off, water molds and the like as is typical of carnations.

*Temperature tolerance.*—Wide range.

Foliage: (base of plant):

*Color.*—Upper side: Near 136A. Lower side: Near 137A.

*Size.*—About 3¼ inches long and about 7/16 inch wide.

*Leaf base and apex.*—Leaf base edge smooth, color near 138D; leaf apex edge smooth, color near 136A.

*Quantity.*—Numerous.

*Shape.*—Lanceolate.

*Texture.*—Smooth.

*Ribs.*—Central keel.

*Arrangement.*—Bi-lateral along stem.

*Stem.*—Color: Near 138C. Size: Stem diameter about ¼ inch.

*Bud.*—Shape: Ovoid. Color: Near 138B. Length: About 1 inch. Diameter: About ⅝ inch.

*Calyx.*—Sepals: About 5. Length: About ¼ inch. Width: About ¼ inch. Color Outside: Near 138B. Inside: Near 138C.

Bloom:

*Shape.*—Rounded.

*Size.*—Diameter: About 2⅛ inches. Depth: About 1 inch.

*Borne.*—As a spray.

*Color.*—General tonality: Light yellow picotee pink. Upper side: Near 2C. Lower side: Near 2D. Center: Near 2C. Outer petals: Near 52C.

*Permanence.*—Dry up on receptacle.

*Keeping quality.*—Very good, about 3 weeks.

*Fragrance.*—Slight.

Petalage:

*Quantity.*—Average between 39 to 40.

*Outer petal size.*—Length: About 1¾ inches. Width: About 1⅝ inches.

*Central petal size.*—Length: About 1⅜ inches. Width: About ¾ inch.

*Texture.*—Smooth.

*Appearance.*—Shiny, petal edge finely serrated, color near 52C in a diffuse picotee pattern of 1/16 inch width with occasional spots near 80A and fine radial lines on a background of near 2C.

*Form.*—Fan shaped.

Reproductive organs:

*Stamen.*—None.

*Anthers.*—None.

*Filaments.*—None.

*Pistil.*—3. Length: About 1⅜ inches. Color: Whiter than 155D.

*Stigma.*—1. Color: Whiter than 155D.

*Fertility.*—Male: Sterile. Female: Good.

*Ovary.*—Shape: Conical. Color. Base: Near 145D. Body: Near 146D. Apex: Near 146D.

*Fruit.*—No fruit or seed produced.

I claim:

1. A new and distinct carnation plant of the variety substantially as herein shown and described.

* * * * *

TinCan Chester Color Reduction Chart